United States Patent
Cowart et al.

(10) Patent No.: US 11,890,407 B2
(45) Date of Patent: Feb. 6, 2024

(54) NEGATIVE PRESSURE WOUND THERAPY CANISTER CONNECTION SYSTEM

(71) Applicant: DeRoyal Industries, Inc., Powell, TN (US)

(72) Inventors: Walter Cleveland Cowart, Blaine, TN (US); Scott Douglas Barnes, Knoxville, TN (US); Vincent Denis Jardret, Powell, TN (US); Jonathan Matthew Cayce, Knoxville, TN (US); Dhanvin Sunil Desai, Knoxville, TN (US); Joe Lowell Smith, Powell, TN (US); Breanna Julia Rhyne, Powell, TN (US)

(73) Assignee: DeRoyal Industries, Inc., Powell, TN (US)

( * ) Notice: Subject to any disclaimer, the term of this patent is extended or adjusted under 35 U.S.C. 154(b) by 292 days.

(21) Appl. No.: 17/193,996

(22) Filed: Mar. 5, 2021

(65) Prior Publication Data
US 2021/0275732 A1    Sep. 9, 2021

Related U.S. Application Data

(60) Provisional application No. 62/985,502, filed on Mar. 5, 2020.

(51) Int. Cl.
*A61M 1/00* (2006.01)

(52) U.S. Cl.
CPC .............. *A61M 1/86* (2021.05); *A61M 1/962* (2021.05); *A61M 1/98* (2021.05); *A61M 1/64* (2021.05)

(58) Field of Classification Search
CPC ......... Y10S 229/91; A61M 1/60; A61M 1/64; A61M 1/98; A61M 2209/086; A61M 2209/084; A61M 1/92; A61M 1/90; A61M 1/72
See application file for complete search history.

(56) References Cited

U.S. PATENT DOCUMENTS

| | | |
|---|---|---|
| 8,251,979 B2 | 8/2012 | Malhi |
| 9,155,821 B2 | 10/2015 | Wudyka |
| 2009/0005746 A1 | 1/2009 | Nielsen et al. |
| 2009/0240218 A1* | 9/2009 | Braga ................... A61M 1/984 604/313 |

(Continued)

OTHER PUBLICATIONS

Digital Picture understood to be the NPWT Canister for Smith & Nephew's Renasys Go system.

(Continued)

*Primary Examiner* — Erich G Herbermann
*Assistant Examiner* — Seth Han
(74) *Attorney, Agent, or Firm* — Luedeka Neely, P.C.

(57) ABSTRACT

A canister connection system for a negative pressure wound therapy system. The canister connection system includes an attachment fixture removably connected to a pump unit. The attachment fixture includes a first engaging mechanism disposed adjacent its first end configured to engage a corresponding first engaging mechanism of the canister and a second engaging mechanism disposed adjacent its second end for engaging a corresponding second engaging mechanism of the canister for removably connecting the canister to the pump unit.

19 Claims, 7 Drawing Sheets

(56) References Cited

U.S. PATENT DOCUMENTS

| | | | |
|---|---|---|---|
| 2010/0185164 A1* | 7/2010 | Hartwell | A61M 1/60 604/319 |
| 2012/0289914 A1* | 11/2012 | Eckstein | A61M 1/74 604/319 |
| 2019/0201595 A1 | 7/2019 | Jardret et al. | |
| 2019/0275219 A1* | 9/2019 | Ehlert | A61M 3/0258 |
| 2019/0358372 A1* | 11/2019 | Askem | A61M 1/912 |
| 2020/0085627 A1 | 3/2020 | Jardret et al. | |

OTHER PUBLICATIONS

International Search Report and Written Opinion for PCT/US2021/021220, dated May 25, 2021, 8 pages.

* cited by examiner

NEGATIVE PRESSURE WOUND THERAPY CANISTER CONNECTION SYSTEM

CROSS REFERENCE TO RELATED APPLICATIONS

This application claims priority to U.S. Provisional Application Ser. No. 62/985,502 filed Mar. 5, 2020, entitled "Negative Pressure Wound Therapy Canister Connection System," the entire contents of which is incorporated herein by reference.

The present disclosure relates to a canister and corresponding canister connection system for a negative pressure wound therapy (NPWT) system. An exemplary NPWT system in which the present disclosure may be implemented is described in U.S. application Ser. No. 16/235,113 filed on Dec. 28, 2018, entitled "Negative Pressure Wound Therapy System," and published as U.S. Publication No. 2019/0201595, the entire contents of which is incorporated herein by reference in its entirety.

While the canister and corresponding canister connection system of the present disclosure may be incorporated into various NPWT systems, the canister shown and described herein is particularly suited to be used in combination with a dual lumen system as described in the '113 Application noted above as well as in combination with the dual lumen tubing connection system described in U.S. application Ser. No. 16/575,770 filed on Sep. 9, 2019, entitled "Tubing Connection System for Negative Pressure Wound Therapy," and published as U.S. Publication No. 2020/0086017, the entire contents of which also being incorporated herein by reference in its entirety.

FIELD

This disclosure relates to the field of negative pressure wound therapy. More particularly, this disclosure relates to a connection system for connecting a collection canister to a vacuum pump.

BACKGROUND

The purpose of negative pressure wound therapy (NPWT) is to apply a reduced pressure (also referred to as negative or vacuum pressure) to a wound to stimulate healing and remove excess exudate from the wound bed. During NPWT, the wound exudate removed from the wound bed is deposited in an exudate collection canister that is often removably secured to the NPWT unit containing the vacuum pump. The connection between the NPWT unit and the collection canister needs to be airtight as well as easy to connect and disconnect. Two of the common complaints from medical staff using NPWT devices are that it is sometimes difficult to know when the canister is securely attached to the device and ready for therapy to be initiated and that the canister is difficult to attach or remove from the unit.

What is needed therefore is a NPWT canister connection system that is quick and easy to connect and disconnect from the NPWT unit. It is also desirable to provide such a canister connection system that provides immediate feedback to the user when the canister is securely attached to the NPWT unit.

SUMMARY

The above and other needs are met by a canister connection system for a negative pressure wound therapy system. The canister connection system includes an attachment fixture for removably connecting to a pump connection wall of a pump unit, the pump connection wall having a first side, a second side, and at least a pump inlet port disposed between the first side and the second side. The attachment fixture includes a first end configured to be disposed adjacent the first side of the pump connection wall, a second end configured to be disposed adjacent the second side of the pump connection wall, a first canister engaging mechanism disposed adjacent the first end of the attachment fixture, and a second canister engaging mechanism disposed adjacent the second end of the attachment fixture. The canister connection system further includes a canister having a canister connection wall having a first side, a second side, and at least a first aperture positioned and configured to be fluidly coupled to the pump inlet port when the canister is connected to the pump unit, a first pump engaging mechanism disposed adjacent the first side of the canister connection wall for removably engaging the first canister engaging mechanism of the attachment fixture, and a second pump engaging mechanism disposed adjacent the second side of the canister connection wall for removably engaging the second canister engaging mechanism of the attachment fixture.

According to certain embodiments, the first canister engaging mechanism is a clip dimensioned and configured to extend out from the pump connection wall, the first pump engaging mechanism is a slot dimensioned and configured to receive the clip for securing the first side of the canister connection wall to the first side of the pump connection wall, the second canister engaging mechanism is a latch receptacle dimensioned and configured to extend out from the pump connection wall in a direction generally perpendicular to the clip, and the second pump engaging mechanism is a depressible latch dimensioned and configured to be inserted into the latch receptacle for securing the second side of the canister connection wall to the second side of the pump connection wall.

According to certain embodiments, the pump connection wall is inset compared to an outer periphery of the pump unit and the canister includes a flange extending out from the canister connection wall for positioning around the inset of the pump connection wall when the canister is connected to the pump unit. In some embodiments, the first canister engaging mechanism of the attachment fixture is a clip dimensioned and configured to extend out from the pump connection wall substantially equal to the outer periphery of the pump unit. In some embodiments, the canister is formed from two molded parts with the two molded parts including a canister plate configured to be secured to a canister body. The canister plate includes the canister connection wall, the flange, the first pump engaging mechanism, and the second pump engaging mechanism.

According to certain embodiments, the canister connection system includes the pump unit and the pump connection wall further includes a resilient seal disposed around the pump inlet port, the resilient seal being dimensioned and configured to press against the canister connection wall when the canister is connected to the pump unit.

According to certain embodiments, the pump connection wall further includes a pump outlet port and the canister connection wall includes a second aperture positioned and configured to be fluidly coupled to the pump outlet port when the canister is connected to the pump unit. In some embodiments, the canister connection system includes the pump unit and the pump connection wall further includes a first resilient seal disposed around the pump inlet port and a second resilient seal disposed around the pump outlet port, the first and second resilient seals dimensioned and configured to press against the canister connection wall when the canister is connected to the pump unit. In some embodiments, the canister includes a collection chamber fluidly coupled to the first aperture and a secondary pressure chamber fluidly coupled to the second aperture that is fluidly isolated from the collection chamber. In some embodiments, a first filter is positioned around the first aperture on an inside surface of the canister connection wall and a second filter is positioned around the second aperture on the inside surface of the canister connection wall.

According to another embodiment of the disclosure, a canister for connecting to a pump unit of a negative pressure wound therapy system includes a canister connection wall having a first side, a second side, and at least a first aperture disposed between the first side and the second side of the canister connection wall. A first pump engaging mechanism is disposed adjacent the first side of the canister connection wall for removably engaging a first canister engaging mechanism disposed adjacent a first side of a pump connection wall of the pump unit. A second pump engaging mechanism is disposed adjacent the second side of the canister connection wall for removably engaging a second canister engaging mechanism disposed adjacent a second side of the pump connection wall of the pump unit. When the first pump engaging mechanism engages the first canister engaging mechanism and the second pump engaging mechanism engages the second canister engaging mechanism, the canister is substantially fluidly sealed to the pump unit and the first aperture is fluidly coupled to a pump inlet port disposed between the first side and the second side of the pump connection wall.

According to certain embodiments, the first canister engaging mechanism is a clip dimensioned and configured to extend out from the pump connection wall, the first pump engaging mechanism is a slot dimensioned and configured to receive the clip for securing the first side of the canister connection wall to the first side of the pump connection wall, the second canister engaging mechanism is a latch receptacle dimensioned and configured to extend out from the pump connection wall in a direction generally perpendicular to the clip, and the second pump engaging mechanism is a depressible latch dimensioned and configured to be inserted into the latch receptacle for securing the second side of the canister connection wall to the second side of the pump connection wall.

According to certain embodiments, the canister includes a flange extending out from the canister connection wall for positioning around the pump connection wall when the canister is connected to the pump unit. In some embodiments, the canister connection wall includes a flat surface with the flange extending out from the flat surface. In some embodiments, the canister is formed from two molded parts, the two molded parts including a canister plate configured to be secured to a canister body with the canister plate including the canister connection wall, the flange, the first pump engaging mechanism, and the second pump engaging mechanism.

According to certain embodiments, the canister further includes a second aperture disposed between the first side and the second side of the canister connection wall, the second aperture positioned and configured to be fluidly coupled to a pump outlet port of the pump connection wall when the canister is connected to the pump unit. In some embodiments, the canister includes a collection chamber fluidly coupled to the first aperture and a secondary pressure chamber fluidly coupled to the second aperture that is fluidly isolated from the collection chamber. In some embodiments, the canister includes a first filter positioned around the first aperture on an inside surface of the canister connection wall and a second filter positioned around the second aperture on the inside surface of the canister connection wall.

According to another embodiment of the disclosure, a method for connecting a canister to a pump connection wall of a pump unit of a negative pressure wound therapy system includes providing a canister having a canister connection wall with a first side, a second side, and at least a first aperture disposed between the first side and the second side of the canister connection wall, a first pump engaging mechanism disposed adjacent the first side of the canister connection wall, and a second pump engaging mechanism disposed adjacent the second side of the canister connection wall. The method further includes engaging the first pump engaging mechanism of the canister with a first canister engaging mechanism disposed adjacent a first side of the pump connection wall such that the first aperture of the canister connection wall is aligned with a pump inlet port of the pump unit and engaging the second pump engaging mechanism of the canister with a second canister engaging mechanism disposed adjacent a second side of the pump connection wall for removably connecting the canister to the pump unit such that canister is substantially fluidly sealed to the pump unit and the first aperture of the canister connection wall is fluidly coupled to the pump inlet port of the pump unit.

In certain embodiments, the method further includes providing an attachment fixture for removably connecting to the pump connection wall, the attachment fixture including a first end configured to be disposed adjacent the first side of the pump unit and a second end configured to be disposed adjacent the second side of the pump unit, the attachment fixture including the first container engaging mechanism disposed adjacent the first end of the attachment fixture and the second container engaging mechanism disposed adjacent the second end of the attachment fixture.

In certain embodiments, the first canister engaging mechanism is a clip dimensioned and configured to extend out from the pump connection wall, the first pump engaging mechanism is a slot dimensioned and configured to receive the clip for securing the first side of the canister connection wall to the first side of the pump connection wall, the second canister engaging mechanism is a latch receptacle dimensioned and configured to extend out from the pump connection wall in a direction generally perpendicular to the clip, and the second pump engaging mechanism is a depressible latch dimensioned and configured to be inserted into the latch receptacle for securing the second side of the canister connection wall to the second side of the pump connection wall.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
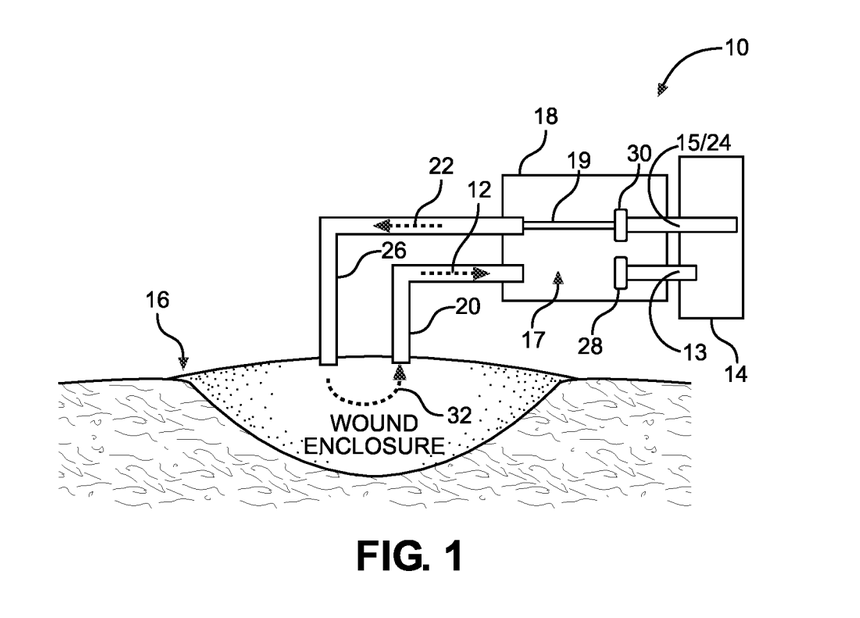
FIG. 1 depicts a functional block diagram of a NPWT system according to one embodiment of the disclosure.

Referring to FIG. 1, an exemplary NPWT system 10 is schematically depicted having two fluidly connected fluid flow paths. According to a first fluid flow path (indicated by arrow 12), a primary pressure source 14 (also referred to herein as a vacuum pump) is operable to provide a primary reduced pressure to a wound enclosure 16 via pump inlet 13 such that fluid flows from the wound enclosure 16 to a collection canister 18 through a first lumen 20. The primary reduced pressure generated by the primary pressure source 14 serves both to stimulate healing by applying the reduced pressure to the wound site and removing exudate from the wound enclosure 16 to the canister 18. According to a second fluid flow path (indicated by arrow 22), a secondary pressure source 24 is operable to provide a secondary pressure to the wound enclosure 16 through second lumen 26. As described in detail in U.S. application Ser. No. 16/235,113, the second fluid flow path 22 is fluidly connected to the first fluid flow path 12 via the wound enclosure 16 such that fluid from the second fluid flow path 22 is pushed into the first lumen 20 to form a converged fluid flow path (as indicated by arrow 32) when both the primary reduced pressure and secondary pressure are delivered to the wound enclosure 16. The converged fluid flow path 32 may be used to facilitate flow of the exudate from the wound site to the canister 18 through the first lumen 20.

In certain embodiments, and as depicted in FIG. 1, vacuum pump 14 may serve as both the primary reduced pressure source and the secondary pressure source 24. According to this embodiment, the inlet 13 of the vacuum pump 14 is fluidly connected to the first lumen 20 with a collection chamber 17 of the canister 18 disposed therebetween such that fluid/exudate collected from the wound enclosure 16 is deposited in the collection chamber 17 of canister 18. On the other hand, the outlet 15 of the vacuum pump 14 is fluidly connected to the second lumen 26 via a secondary pressure chamber 19 that traverses the interior of canister 18 while being fluidly isolated from the collection chamber 17. In other words, the secondary pressure chamber 19 extends through the canister 16 for fluidly connecting the outlet 15 to the second lumen 22 and isolating the secondary pressure generated by the pump outlet 15 from the reduced pressure generated from the pump inlet 13).

Still referring to FIG. 1, canister 18 preferably includes at least a first filter 28 disposed between the pump inlet 13 and the collection chamber 17 and a second filter 30 disposed adjacent the pump outlet 15 and within secondary pressure chamber 19. The first filter 28 is positioned and configured for protecting the vacuum pump 14 from exudate collected in the collection chamber 17 by preventing exudate from entering the vacuum pump 14 through the pump inlet 13.

The second filter 30 is positioned and configured for removing undesirable particulates generated by the pump outlet 15. Accordingly, using appropriate filters 28 and 30 in combination with the pump inlet 13 as the primary pressure source 14 and the pump outlet 15 as the secondary pressure source 24, the NPWT system 10 of FIG. 1 may be used to create an active circulation of air flow between the canister 18 and the wound enclosure 16 using a single vacuum pump.

Figure 2:
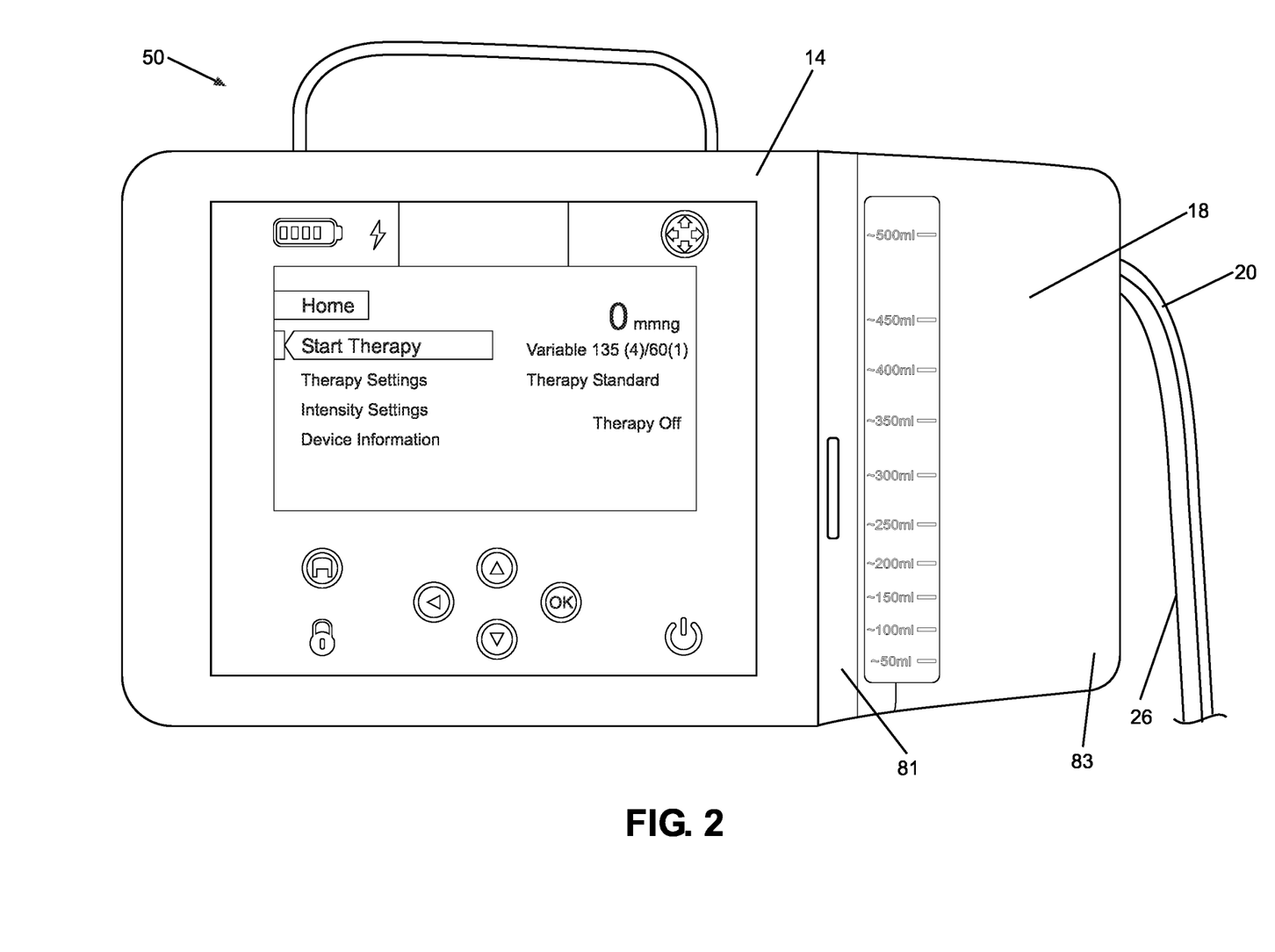
FIG. 2 depicts a front view of a NPWT unit with a cannister secured to a vacuum pump according to one embodiment of the disclosure.
Figure 3:
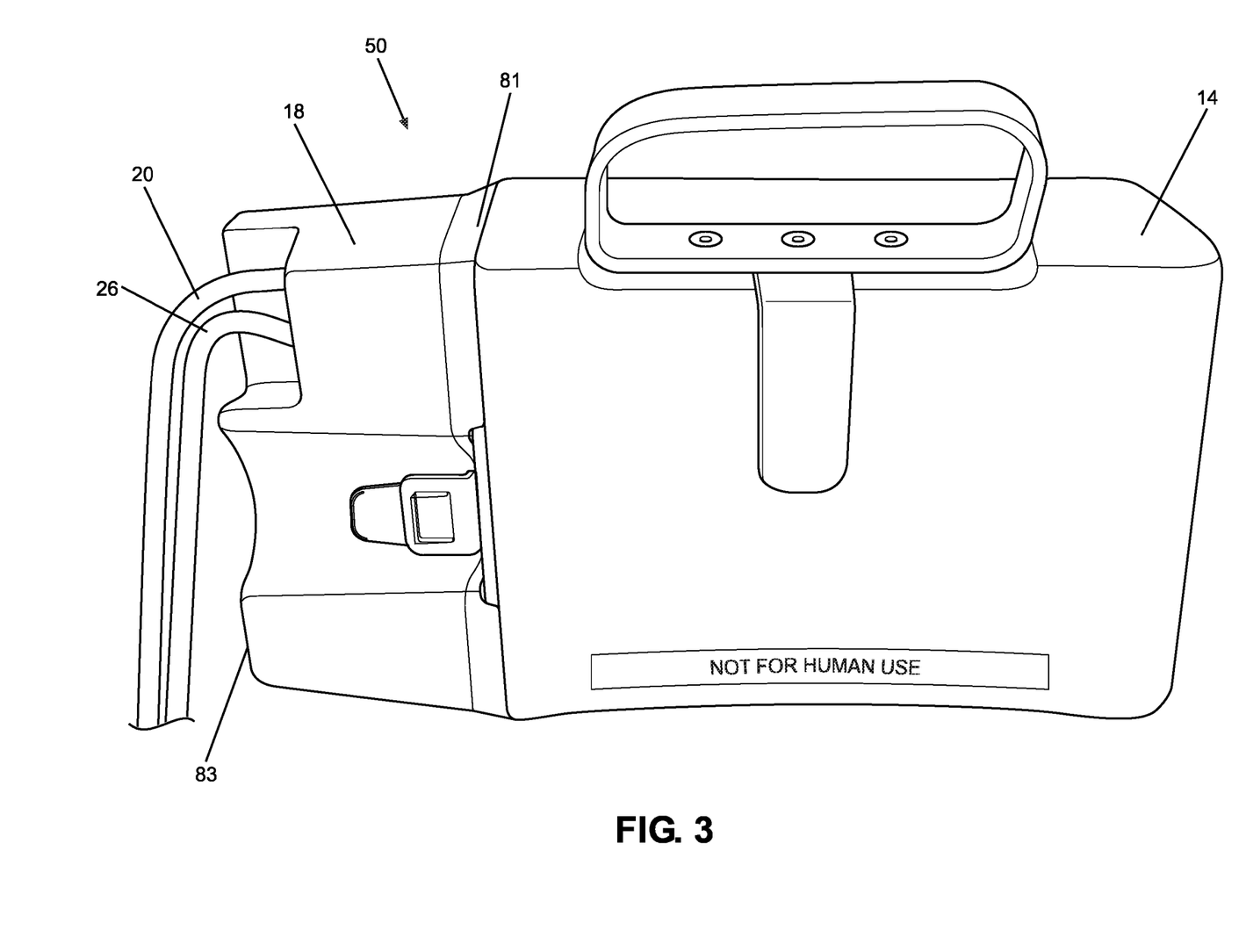
FIG. 3 depicts a rear view of the NPWT unit of FIG. 2.

With reference to FIGS. 2-3, the present disclosure is generally directed to a connection system for removably connecting a first end 81 of collection canister 18 to a corresponding end of vacuum pump unit 14 to form NPWT unit 50. When the canister 18 is appropriately connected to the pump unit 14 as shown in FIGS. 2-3, and with reference back to the schematic of FIG. 1, the pump inlet 13 is fluidly coupled to a first lumen 20 connected to the second end 83 of canister 18 for providing reduced pressure to a wound site. Similarly, in embodiments in which the pump outlet 15 is used as a secondary pressure source, the pump outlet 15 is fluidly coupled to a second lumen 26 also connected to the second end 83 of canister 18 for providing secondary pressure to the wound site.

Figure 4:
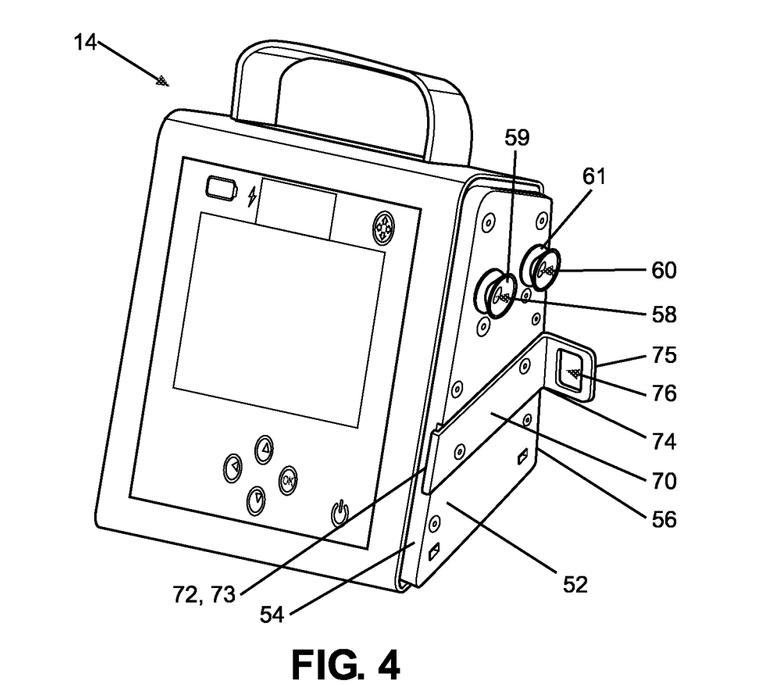
FIG. 4 depicts a front perspective view of a pump connection wall of a vacuum pump according to one embodiment of the disclosure.
Figure 5:
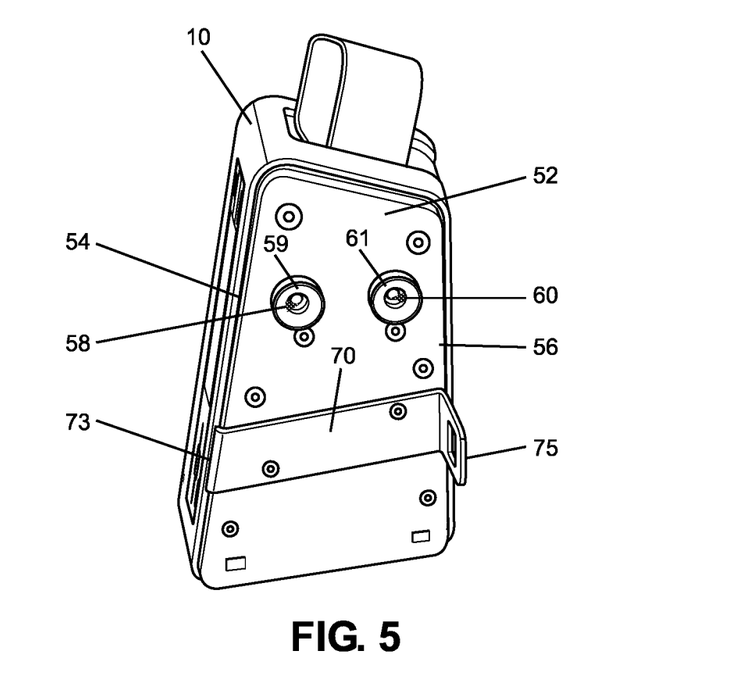
FIG. 5 depicts a side perspective view of the pump connection wall of FIG. 4.

More specifically, and with reference to FIGS. 4-5, vacuum pump unit 14 includes a pump connection wall 52 having a first side 54 and a second side 56. Disposed between the first side 54 and the second side 56 is a pump inlet port 58 in fluid communication with the pump inlet 13. A seal 59 is preferably disposed around the pump inlet port 58. In embodiments in which the pump outlet 15 is used as a secondary pressure source 24, such as described above with respect to FIG. 1, the connection wall 52 further includes a pump outlet port 60 in fluid communication with the pump outlet 15. A seal 61 is preferably disposed around the pump outlet port 60.

With continued reference to FIGS. 4-5, pump connection wall 52 further includes an attachment fixture 70 that extends from the first side 54 to the second side 56 of the connection wall 52. In preferred embodiments, the attachment fixture 70 is removably connected to the connection wall 52 such that attachment fixture 70 is able to be easily replaced as needed (e.g., when the engaging mechanisms described below are damaged/worn such that a proper connection is prevented or if it is desired to use an attachment fixture 70 with differently configured engaging mechanisms). The pump connection wall 52 also preferably includes a slight recess that is dimensioned and configured to receive the attachment fixture 70 such that the body of the attachment fixture 70 is flush with the rest of the pump connection wall 52 when the attachment fixture 70 is connected to the pump connection wall as depicted in FIGS. 4-5.

Attachment fixture 70 includes a first end 72 that is disposed adjacent the first side 54 of pump connection wall 52 and a second end 74 disposed adjacent the second side 56 of pump connection wall 52. The attachment fixture 70 further includes a first engaging mechanism 73 disposed adjacent the first end 72 and a second engaging mechanism 75 disposed adjacent the second end 74. In preferred embodiments, the first engaging mechanism 73 is in the form of a clip dimensioned and configured to extend out from the pump connection wall 52 towards the front of the unit 14 while the second engaging mechanism 75 is in the form of a latch receptacle having opening 76 extending out from the pump connection wall 52 in a direction generally perpendicular to the first engaging mechanism 73. While the attachment fixture 70 is preferably a unitary piece as depicted in the present application, it should be understood that the attachment fixture could be formed from multiple portions. For example, a first portion of attachment fixture 70 could include the first engaging mechanism 73 while a second portion of the attachment fixture 70 could include the second engaging mechanism 75.

Figure 6:
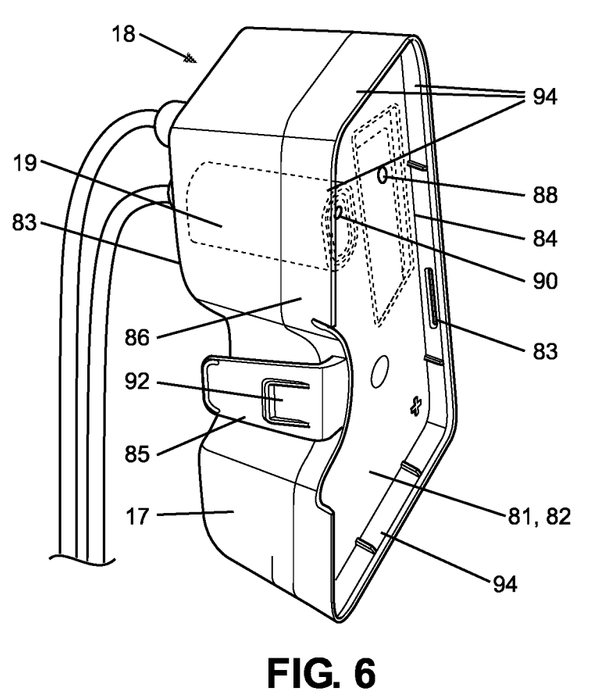
FIG. 6 depicts a side perspective view of a cannister connection wall of a canister according to one embodiment of the disclosure.
Figure 7:
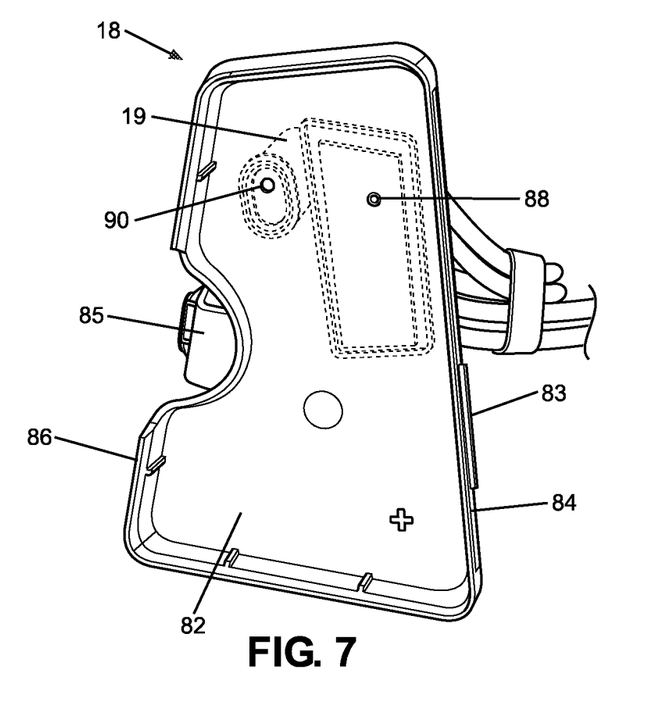
FIG. 7 depicts a side elevational view of the cannister connection wall of FIG. 6.

Referring to FIGS. 6-7, canister 18 includes a canister connection wall 82 at the first end 81 of canister 18. The canister connection wall 82 is configured to be disposed adjacent to and align with the pump connection wall 52 when the canister 18 is fluidly connected to the vacuum pump unit 14. Disposed between a first side 84 of the canister connection wall 82 and a second side 86 of the canister connection wall 82 is a first aperture 88 positioned to be fluidly coupled and aligned with the pump inlet port 58 and a second aperture 90 positioned to be fluidly coupled and aligned with the pump outlet port 60 when the canister 18 is fluidly connected to the vacuum pump unit 14. As described above with respect to FIG. 1, canister 18 further includes a collection chamber 17 disposed between the first end 81 and the second end 83 of the canister 18 that is fluidly coupled with the first aperture 88 of the canister connection wall 82 and a secondary pressure chamber 19 that is fluidly coupled to the second aperture 90 of the canister connection wall 82 and traverses the interior of canister while being isolated from the collection chamber 17. Appropriate tubing connections may then be provided at the second end 83 of the canister 18 to complete the first fluid flow path 12 and second fluid flow path 22 from canister 18 to the wound enclosure 16 as depicted in FIG. 1.

With continued reference to FIGS. 6-7, canister connection wall 82 includes a first engaging mechanism 83 disposed adjacent the first side 84 of canister connection wall 82 that is positioned and configured to engage the first engaging mechanism 73 of the attachment fixture 70 when securing the canister 18 to the vacuum pump unit 14. Disposed adjacent a second side 86 of the canister connection wall 82 is a second engaging mechanism 85 positioned and configured to engage the second engaging mechanism 75 of the attachment fixture 70 when securing the canister 18 to the vacuum pump unit 14.

As noted above, the first engaging mechanism 73 of the attachment fixture 70 is preferably in the form of a clip while the second engaging mechanism 75 is in the form of a latch receptacle. Thus, according to this embodiment, the first engaging mechanism 83 of the canister 18 is a clip receiver in the form of a slot dimensioned and configured to receive the clip 73 of the attachment fixture 70 while the second engaging mechanism 85 of the canister 18 is a depressible latch 85 having a tab 92 that is configured to engage and removably lock to the latch receptacle 75 of the attachment fixture 70.

Figure 8A:
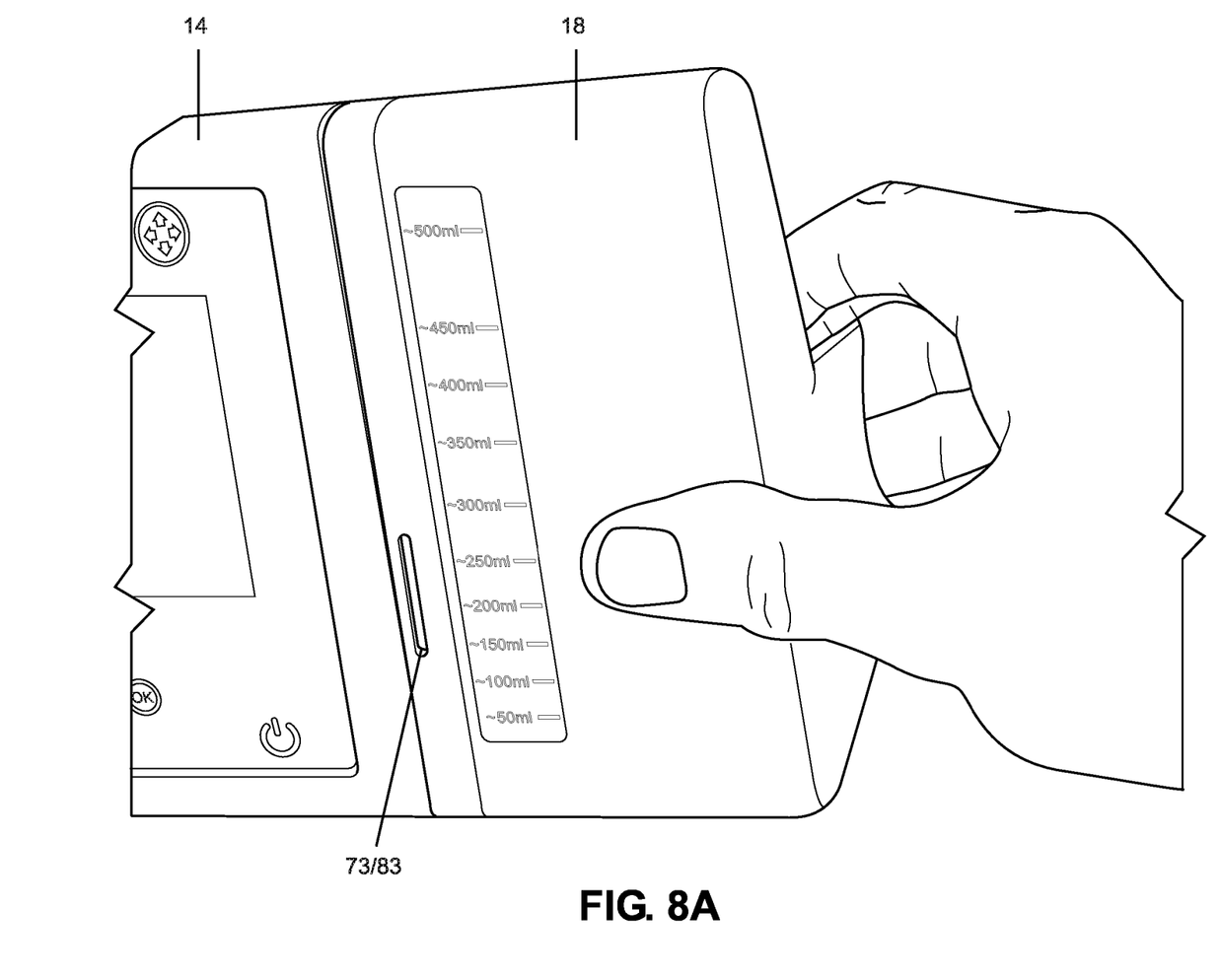
FIGS. 8A-8C depict a sequence of steps for securing a canister to a vacuum pump according to one embodiment of the disclosure.
Figure 8B:
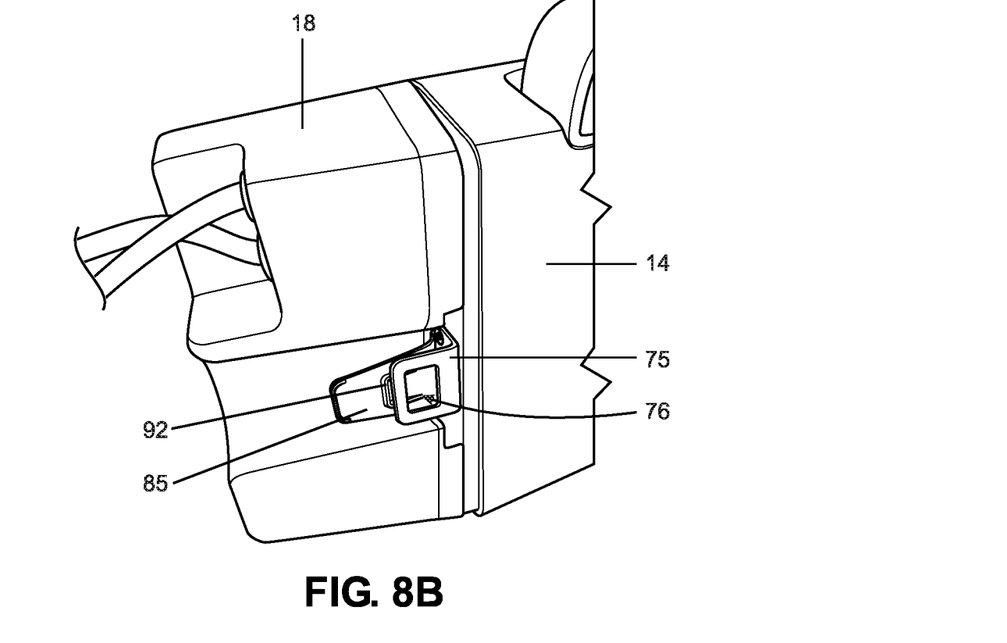
Figure 8C:
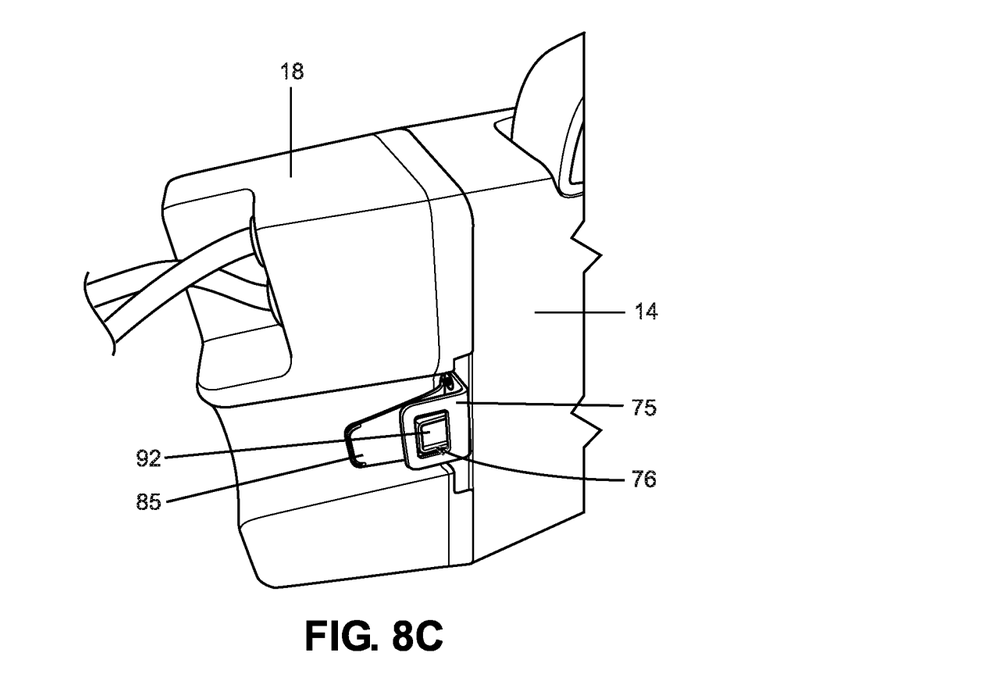

Referring to FIGS. 8A-8C, the preferred operation of securing the canister 18 to the vacuum pump 14. Referring to FIG. 8A, the user/caregiver first positions the canister 18 such that the clip 73 of the attachment fixture 70 is inserted through the clip receiver/slot 83 as shown in the front view of FIG. 9. It should be understood that this aligns the cannister connection wall 82 with the pump connection wall 52 and, similarly, the depressible latch 85 of the canister 18 with the latch receptacle 75 of the attachment fixture 70. With reference to FIG. 8B, the canister 18 is then pushed towards the pump connection wall 52 such that the tab 92 of the depressible latch 85 is deflected inward by the latch receptacle 75. In this regard, the tab 92 preferably includes a ramped surface. As the ramped surface traverses the latch receptacle 75, the tab 92 is able to gradually flex inward until the tab 92 reaches the opening 76 of the latch receptacle 75. With reference to FIG. 8C, once the tab 92 reaches the opening 76 of the latch receptacle 75, the depressible latch 85 snaps back towards its resting position to lock the canister 16 to the pump 14 and provide an audible click when the depressible latch 85 surface contacts the surface of the attachment fixture 70 disposed around the latch opening 76. To remove the canister 15 from the vacuum pump 14, the depressible latch 85 is pushed inward to disengage the tab 92 from the latch receptacle 75.

Accordingly, the engagement of the attachment fixture clip 73 to the slot 83 of the canister 18 is intended to retain the first side 84 of the canister connection wall 82 against the first side 54 of the pump connection wall 52 while the engagement of the canister latch 85 with the latch receptacle 75 of the attachment fixture 70 is intended to retain the second side 86 of the canister connection wall 82 against the second side 56 of the pump connection wall 52. According to another aspect of the disclosure, the resilient seals 59 and 61 around the apertures 58 and 60 of the pump connection wall 52 are dimensioned and configured to press against the cannister connection wall 82 when the canister 18 is connected to the pump unit 14. The combination of countering forces from the seals 59 and 61 in one direction, and the engagement of the engaging mechanisms of the canister 18 and pump unit 14 in the other direction maintain the canister 18 in place against the pump unit 14 and provide for an air tight connection between the two units and the fluid flow paths established by the connected system 50.

According to another aspect and the disclosure, and with reference to FIGS. 4-5, the pump connection wall 52 is preferably inset slightly as compared to the outer periphery of the rest of the pump unit 14 (see FIGS. 2-4). The clip 73 then preferably extends from the attachment fixture 70 equal to the outer periphery of the pump unit 14. With reference to FIG. 6, the canister 18 includes a flange 94 extending from the cannister connection wall 82. Thus, when the canister 18 is secured to the vacuum pump 14, the flange 94 of the canister 18 provides a consistent outer periphery as shown best in FIGS. 2-3 and helps to provide an air tight seal when the canister 18 is connected to the pump unit 14. In preferred embodiments, the engaging mechanism 83 of the canister 18 is disposed within the flange 94 as shown best in FIG. 6.

According to certain embodiments, the clip 73 of attachment fixture 70 is in the shape of a relatively thin and elongated blade. According to this embodiment, the slot 83 is a generally oblong slot for receiving the blade shape of the clip 73. However, it should be understood that other shapes of the clip 73 and slot 83 are possible and within the scope of the present disclosure.

As shown in the present figures, the latch 85 of the canister 18 and latch receptacle 75 of the attachment fixture are intended to be positioned on the rear side of the combined unit 50 while the clip 73 and slot 83 are positioned on the front side of the combined unit 50. However, it should be understood that these positions could be reversed within the scope of the present disclosure.

According to certain embodiments, the canister 18 is formed molded from two parts with the first part being the canister body and the second part being a canister plate that includes the canister connecting wall 82 with extending flange 94 containing the slot 83 within one portion of the flange 94 and the depressible latch 85 extending from one portion of the flange 94 generally opposite the slot 83. According to certain embodiments, the two parts are secured onto each other with a light curable adhesive such that the canister connection wall 82 covers the canister body.

According to preferred embodiments, the engaging mechanisms 83 and 85 of the canister plate are molded into the shape of the canister plate to enable efficient manufacturing of the disposable canisters. However, it should be understood that the engaging mechanisms could also be formed by separate parts intended to be secured to the canister plate.

According to certain embodiments, a first anti-bacterial filter is positioned around the first aperture 88 on the inside surface of the canister connection wall 82. As described above with respect to filter 28 of FIG. 1, the first filter is positioned and configured to protect the vacuum pump 14 from exudate collected in the collection chamber 17 by preventing exudate from entering the vacuum pump 14 through the pump inlet 13. A second anti-bacterial filter may then be positioned around the second aperture 90 on the inside surface of the canister connection wall 82 (i.e., on the inside surface of the secondary pressure chamber 19). As described above with respect to filter 30 of FIG. 1, the second filter is positioned and configured for removing undesirable particulates generated by the pump outlet 15.

According to certain embodiments, the first filter positioned around the first aperture 88 presents a high water-entry-pressure. Preferably, the water-entry-pressure is at least 0.7 atm. According to certain embodiments, the first filter includes an anti-bacterial membrane and an anti-odor material to absorb potential odors. According to certain embodiments, the anti-odor material is carbon based. According to certain embodiments, the first filter presents a very high bacterial filtration efficiency of at least 99.999%.

According to certain embodiments, the latch 85 is conveniently located along the ergonomic shape of the canister 18 such that the user's fingers go naturally over the latch when the user grabs the canister to disconnect it. The user can then press on the latch 85 to release the latch from the receptacle 75 while holding the canister 18 between the thumb on the front of the canister 18, and the fingers along the back of the canister 18 and then slide the canister forward to disengage the clip 73 from the slot 83 located on the front side of the canister.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A canister connection system for a negative pressure wound therapy system, the canister connection system including:
    an attachment fixture for removably connecting to a pump connection wall of a pump unit, the pump connection wall having a first side, a second side, and at least a pump inlet port disposed between the first side and the second side, the attachment fixture including:
        a first end configured to be disposed adjacent the first side of the pump connection wall,
        a second end configured to be disposed adjacent the second side of the pump connection wall,
        a first canister engaging mechanism disposed adjacent the first end of the attachment fixture, and
        a second canister engaging mechanism disposed adjacent the second end of the attachment fixture;
    a canister including:
        a canister connection wall having a first side, a second side, and at least a first aperture positioned and configured to be fluidly coupled to the pump inlet port when the canister is connected to the pump unit,
        a first pump engaging mechanism disposed adjacent the first side of the canister connection wall for removably engaging the first canister engaging mechanism of the attachment fixture, and
        a second pump engaging mechanism disposed adjacent the second side of the canister connection wall for removably engaging the second canister engaging mechanism of the attachment fixture.

2. The canister connection system of claim 1 wherein:
    the first canister engaging mechanism is a clip dimensioned and configured to extend out from the pump connection wall and the first pump engaging mechanism is a slot dimensioned and configured to receive the clip for securing the first side of the canister connection wall to the first side of the pump connection wall; and
    the second canister engaging mechanism is a latch receptacle dimensioned and configured to extend out from the pump connection wall in a direction generally perpendicular to the clip and the second pump engaging mechanism is a depressible latch dimensioned and configured to be inserted into the latch receptacle for securing the second side of the canister connection wall to the second side of the pump connection wall.

3. The canister connection system of claim 1 wherein the pump connection wall is inset compared to an outer periphery of the pump unit and the canister includes a flange extending out from the canister connection wall for positioning around the inset of the pump connection wall when the canister is connected to the pump unit.

4. The canister connection system of claim 3 wherein the first canister engaging mechanism of the attachment fixture is a clip dimensioned and configured to extend out from the pump connection wall substantially equal to the outer periphery of the pump unit.

5. The canister connection system of claim 3 wherein the canister is formed from two molded parts secured together, the two molded parts including a canister plate and a canister body, the canister plate including the canister connection wall, the flange, the first pump engaging mechanism, and the second pump engaging mechanism.

6. The canister connection system of claim 1 wherein the canister connection system includes the pump unit and the pump connection wall further includes a resilient seal disposed around the pump inlet port, the resilient seal being dimensioned and configured to press against the canister connection wall when the canister is connected to the pump unit.

7. The canister connection system of claim 1 wherein the pump connection wall further includes a pump outlet port and the canister connection wall includes a second aperture positioned and configured to be fluidly coupled to the pump outlet port when the canister is connected to the pump unit.

8. The canister connection system of claim 7 wherein the canister connection system includes the pump unit and the pump connection wall further includes a first resilient seal disposed around the pump inlet port and a second resilient seal disposed around the pump outlet port, the first and second resilient seals dimensioned and configured to press against the canister connection wall when the canister is connected to the pump unit.

9. The canister connection system of claim 7 wherein the canister includes a collection chamber fluidly coupled to the first aperture and a secondary pressure chamber fluidly coupled to the second aperture that is fluidly isolated from the collection chamber.

10. The canister connection system of claim 9 including a first filter positioned around the first aperture on an inside surface of the canister connection wall and a second filter positioned around the second aperture on the inside surface of the canister connection wall.

11. A canister for connecting to a pump unit of a negative pressure wound therapy system, the canister comprising:
　a canister connection wall having a first side, a second side, and at least a first aperture and a second aperture disposed between the first side and the second side of the canister connection wall;
　a first pump engaging mechanism disposed adjacent the first side of the canister connection wall for removably engaging a first canister engaging mechanism disposed adjacent a first side of a pump connection wall of the pump unit; and
　a second pump engaging mechanism disposed adjacent the second side of the canister connection wall for removably engaging a second canister engaging mechanism disposed adjacent a second side of the pump connection wall of the pump unit,
　wherein, when the first pump engaging mechanism engages the first canister engaging mechanism and the second pump engaging mechanism engages the second canister engaging mechanism, the canister is substantially fluidly sealed to the pump unit, the first aperture is fluidly coupled to a pump inlet port disposed between the first side and the second side of the pump connection wall, and the second aperture is fluidly coupled to an outlet port of the pump unit disposed between the first side and the second side of the pump connection wall.

12. The canister of claim 11 wherein:
　the first canister engaging mechanism is a clip dimensioned and configured to extend out from the pump connection wall and the first pump engaging mechanism is a slot dimensioned and configured to receive the clip for securing the first side of the canister connection wall to the first side of the pump connection wall; and
　the second canister engaging mechanism is a latch receptacle dimensioned and configured to extend out from the pump connection wall in a direction generally perpendicular to the clip and the second pump engaging mechanism is a depressible latch dimensioned and configured to be inserted into the latch receptacle for securing the second side of the canister connection wall to the second side of the pump connection wall.

13. The canister of claim 11 wherein the canister includes a flange extending out from the canister connection wall for positioning around the pump connection wall when the canister is connected to the pump unit.

14. The canister of claim 13 wherein the canister connection wall includes a flat surface with the flange extending out from the flat surface.

15. The canister of claim 13 wherein the canister is formed from two molded parts secured together, the two molded parts including a canister plate and a canister body, the canister plate including the canister connection wall, the flange, the first pump engaging mechanism, and the second pump engaging mechanism.

16. The canister of claim 11 wherein the canister includes a collection chamber fluidly coupled to the first aperture and a secondary pressure chamber fluidly coupled to the second aperture that is fluidly isolated from the collection chamber.

17. The canister of claim 16 including a first filter positioned around the first aperture on an inside surface of the canister connection wall and a second filter positioned around the second aperture on the inside surface of the canister connection wall.

18. A method for connecting a canister to a pump connection wall of a pump unit of a negative pressure wound therapy system, the method comprising:
　providing an attachment fixture for removably connecting to the pump connection wall of the pump unit, the pump connection wall having a first side, a second side, and at least a pump inlet port disposed between the first side and the second side, the attachment fixture including a first end, a second end, a first canister engaging mechanism disposed adjacent the first end of the attachment fixture, and a second canister engaging mechanism disposed adjacent the second end of the attachment fixture;
　providing a canister including:
　　a canister connection wall having a first side, a second side, and at least a first aperture disposed between the first side and the second side of the canister connection wall,
　　a first pump engaging mechanism disposed adjacent the first side of the canister connection wall, and
　　a second pump engaging mechanism disposed adjacent the second side of the canister connection wall;
　connecting the attachment fixture to the pump connection wall of the pump unit such that the attachment fixture extends from the first side of the pump connection wall to the second side of the pump connection wall with the first end disposed adjacent the first side of the pump connection wall and the second end disposed adjacent the second side of the pump connection wall;
　engaging the first pump engaging mechanism of the canister with the first canister engaging mechanism disposed adjacent the first side of the pump connection wall such that the first aperture of the canister connection wall is aligned with the pump inlet port of the pump unit; and
　engaging the second pump engaging mechanism of the canister with the second canister engaging mechanism disposed adjacent the second side of the pump connection wall for removably connecting the canister to the pump unit such that canister is substantially fluidly sealed to the pump unit and the first aperture of the canister connection wall is fluidly coupled to the pump inlet port of the pump unit.

19. The method of claim 18 wherein:
　the first canister engaging mechanism is a clip dimensioned and configured to extend out from the pump connection wall and the first pump engaging mechanism is a slot dimensioned and configured to receive the clip for securing the first side of the canister connection wall to the first side of the pump connection wall; and
　the second canister engaging mechanism is a latch receptacle dimensioned and configured to extend out from the pump connection wall in a direction generally perpendicular to the clip and the second pump engaging mechanism is a depressible latch dimensioned and configured to be inserted into the latch receptacle for securing the second side of the canister connection wall to the second side of the pump connection wall.

\* \* \* \* \*